United States Patent [19]
Keller

[11] Patent Number: 6,099,569
[45] Date of Patent: Aug. 8, 2000

[54] ENDOPROSTHESIS

[75] Inventor: Arnold Keller, Kayhude, Germany

[73] Assignee: Waldemar Link (GmbH & Co.), Hamburg, Germany

[21] Appl. No.: 09/230,153

[22] PCT Filed: May 7, 1997

[86] PCT No.: PCT/EP97/02344

§ 371 Date: Jan. 19, 1999

§ 102(e) Date: Jan. 19, 1999

[87] PCT Pub. No.: WO98/04215

PCT Pub. Date: Feb. 5, 1998

[30] Foreign Application Priority Data

Jul. 24, 1996 [DE] Germany ............ 296 12 857 U

[51] Int. Cl.[7] .................................................. A61F 2/38
[52] U.S. Cl. ..................... 623/20.15; 623/22.42; 623/23.15
[58] Field of Search ................. 623/20.15, 16, 623/18, 21, 22, 23, 20.2, 20.28, 20.22, 21.13, 21.16, 21.17, 22.42, 22.28, 23.27, 23.22, 23.15

[56] References Cited

U.S. PATENT DOCUMENTS

| | | | |
|---|---|---|---|
| 3,067,740 | 12/1962 | Haboush | 623/23 |
| 4,115,875 | 9/1978 | Rambert et al. | 623/23 |
| 4,129,903 | 12/1978 | Huggler | 623/23 |
| 4,963,155 | 10/1990 | Lazzeri et al. | 623/23 |
| 5,002,578 | 3/1991 | Luman | 623/23 |
| 5,002,581 | 3/1991 | Paxson et al. | 623/23 |
| 5,211,666 | 5/1993 | Fetto | 623/23 |

*Primary Examiner*—Pedro Philogene
*Attorney, Agent, or Firm*—Morrison & Foerster LLP

[57] ABSTRACT

An endoprosthesis adapted for permitting the disconnection of components of the endoprosthesis from one another for the purpose of providing mutual position securing includes a first component having a connection plug and a second component having a connection bore for receiving said connection plug. The first component also has a securing bolt within a bolt bore in the first component, and the second component has a recess formed therein for receiving part of the length of the securing bolt. The securing bolt is brittle or soft or has a predetermined break point selected so that a load that breaks or shears off the securing bolt is of an amplitude not to be expected during normal use of the endoprosthesis.

6 Claims, 1 Drawing Sheet

ENDOPROSTHESIS

Method for disconnecting two components of an endoprosthesis from one another, and endoprosthesis suitable for application of this method

FIELD AND BACKGROUND OF THE INVENTION

Endoprostheses are known (EP-B 474 015) whose components are connected to one another via a cone connection. The latter comprises a conical bore on one component and a conical plug on the other component, the conical plug matching the conical bore and being received by it. When a sufficiently small cone angle is chosen, these fit securely one within the other, as long as they have been joined together with sufficient force at the time of assembly. To safeguard it against chance damage, this cone connection is provided with a securing screw which sits in a threaded bore of one component and can be screwed forwards with its tip into a corresponding recess in the other component transverse to the direction of release. In the event of follow-up surgery, the securing screw is not readily accessible. The removal of the prosthesis which is to be replaced is thus made difficult.

SUMMARY OF THE INVENTION

The invention is therefore based on the object of making it easier to release a securing bolt of this type in the event of follow-up surgery.

The solution according to the invention lies in the method in which the connection is disconnected by the securing bolt being broken or sheared off. To do this, a load is applied which is of an amplitude not to be expected during normal use of the prosthesis. In order to make the breaking or shearing-off easier, the securing bolt is designed brittle or soft or with a predetermined break point.

For example, in the case of a brittle securing bolt, a suitable instrument is used during follow-up surgery to exert an impact on one of the two components in the direction of release, by means of which impact the securing plug is broken, and by means of which impact the connection plug in the connection bore is also generally released at the same time, so that the components can thereafter be easily separated from one another.

A screw bolt is generally used as securing bolt; however, this is not absolutely essential.

To ensure that the broken section of the securing bolt is not jammed between the two components and does not thus impede their separation, a recess should be provided in its proximity, which recess is of sufficient size to receive the broken section. For this purpose, use is expediently made of the recess into which the partial length of the bolt engages in the securing state.

The invention is explained in greater detail hereinbelow with reference to the drawing, which represents advantageous illustrative embodiments and in which:

DETAILED DESCRIPTION OF THE INVENTION

Figure 1:
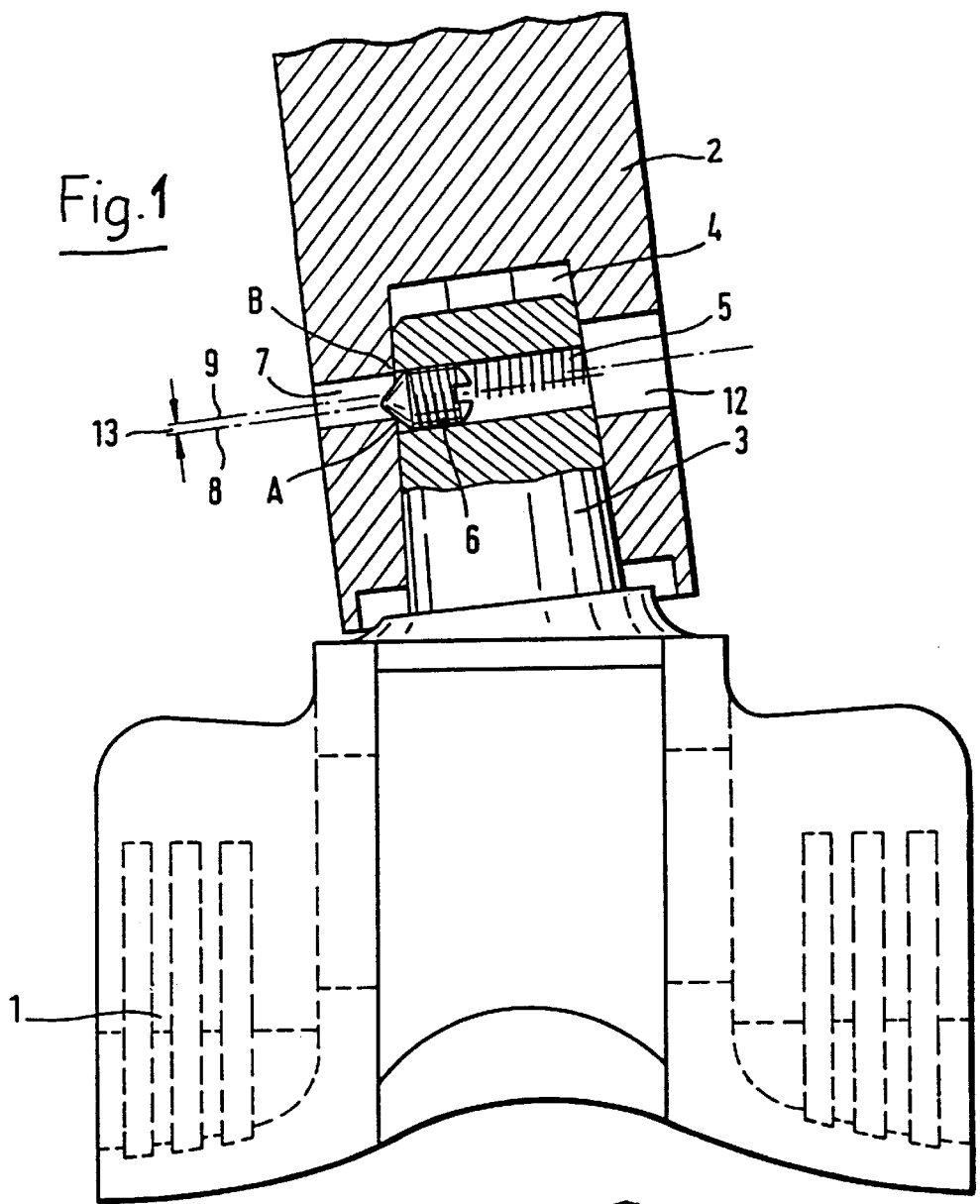
FIG. 1 shows a cone connection between the femoral component of a knee-joint endoprosthesis and the associated medullary cavity plug.

In the embodiment according to FIG. 1, the femoral component 1 of a knee-joint endoprosthesis is connected to a medullary cavity shaft whose lower portion 2 is shown partially cut away. A conical plug 3, which is fitted in a conical bore 4 of the medullary cavity shaft, is connected to the component 1. Inside the conical plug there is a threaded bore 5 which contains a securing screw 6 whose tip can be screwed forwards into a bore 7 which serves as associated securing recess. The axes 8 and 9 of the bores 5 and 7 are offset by the amount 13, so that the tip of the securing screw 6 cooperates with that edge A of the bore 7 lying on the side of the bore 7 in the direction of release. When the screw 6 is tightened, a force strengthening the cone connection 3, 4 is generated. The other edge B of the bore 7 is in normal circumstances not reached by the securing screw.

Before assembly, the securing screw 6 lies completely in the threaded bore 5, so that the cone 3 can be fitted into the bore 4. The securing screw is then accessible via the bore 12 in part 2, so that it can be screwed into the securing position. If so desired, a locking screw (not shown) can then be fitted in order to secure the securing screw 6 in the securing position.

The securing screw 6 consists of brittle material which is nevertheless sufficiently strong to guarantee the securing function during normal use of the prosthesis. In the event of follow-up surgery, a suitable instrument is used to exert an impact on the component 1 in the direction of release. The tip of the securing screw thus breaks off and drops into the bore 7. The parts can then easily be separated from one another.

Alternatively, the securing screw 6 can consist of a soft material whose strength is sufficient for the securing function, but which is nevertheless sheared off if, for example, a force separating the components 1 and 2 is exerted using a spreader instrument.

Figure 2:
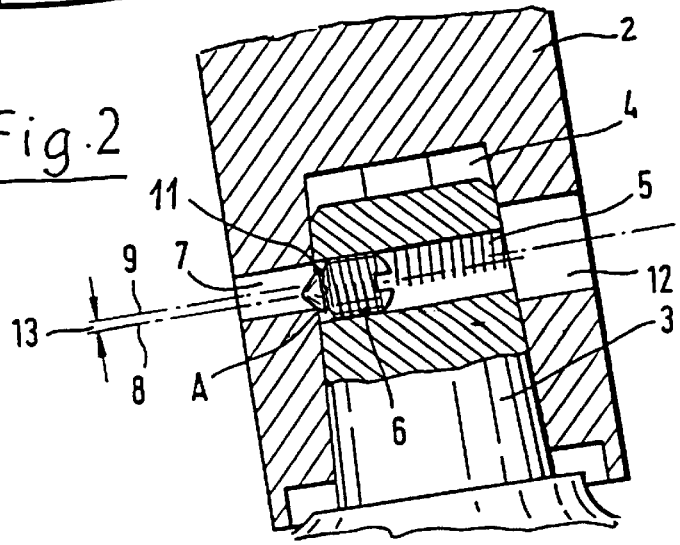
FIG. 2 shows a partial cross-section through the arrangement according to FIG. 1 in an alternative embodiment.

In the alternative embodiment in FIG. 2, whose constructional make-up (where not shown) can be likened to that of FIG. 1, the tip of the securing screw 6, cooperating in a securing function with the bore 7, is separated from the main part of the screw via a predetermined break point 11. This ensures that the broken section, which is formed after the screw tip is broken off or shorn off, is not too large to be received by the bore 7. If a broken section is anticipated to be of a size exceeding the receiving capacity of the bore 7, then the latter can easily be designed wider toward the side of its edge B, since the securing function depends solely on the unchanged edge A.

What is claimed is:

1. An endoprosthesis adapted for permitting disconnecting components of said endoprosthesis from one another for the purpose of providing mutual position securing, wherein said components comprise a first component having a connection plug and a second component having a connection bore for receiving said connection plug, wherein said first component has a securing bolt within a bolt bore in said first component and said second component has a recess formed therein for receiving part of a length of the securing bolt, the securing bolt having a predetermined break point so that a load that breaks or shears off said securing bolt is of an amplitude not to be expected during normal use of the endoprosthesis.

2. The endoprosthesis of claim 1, wherein the recess is of a size sufficient to receive a detached portion of said securing bolt.

3. The endoprosthesis of claim 1, wherein said connection plug has formed therein a threaded bore into which a securing screw can be inserted.

4. The endoprosthesis of claim 3, wherein said second component includes a securing recess into which a tip of said securing screw extends.

5. method for disconnecting components of an endoprosthesis from one another for the purpose of providing mutual position securing, wherein said components comprise a first component having a connection plug and a second component having a connection bore for receiving said connection plug, said method comprising:

providing a securing bolt within a bolt bore in said first component and a recess in said second component for receiving part of a length of the securing bolt; and breaking or shearing off said securing bolt, the securing bolt being brittle or soft or having a predetermined break point so that a load applied to break or shear off said securing bolt is of an amplitude not to be expected during normal use of the endoprosthesis.

6. The method of claim 5, wherein said breaking or shearing off of said securing bolt comprises using an instrument to apply said load in a direction of release.

* * * * *